May 31, 1966 E. S. BOERNER Plant Pat. 2,639
CHRYSANTHEMUM PLANT
Filed June 7, 1965
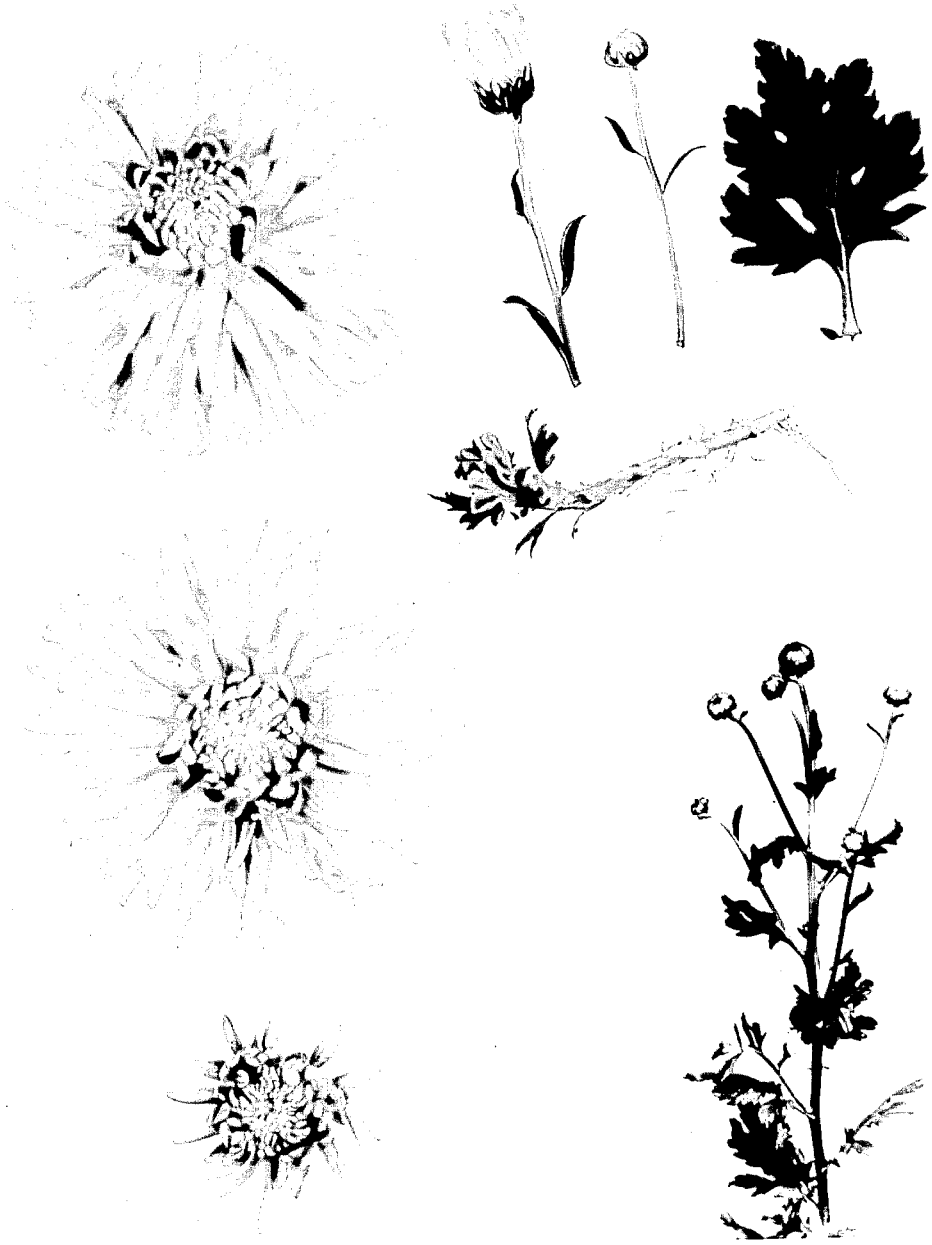
Inventor.
E. S. Boerner
By: Robb & Robb
Attorneys.

United States Patent Office

Plant Pat. 2,639
Patented May 31, 1966

2,639
CHRYSANTHEMUM PLANT

Eugene S. Boerner, Newark, N.Y., assignor to Jackson & Perkins Company, Newark, N.Y., a corporation of New York Filed June 7, 1965, Ser. No. 462,154
1 Claim. (Cl. Plt.—82)

The present invention relates to a new and distinct variety of chrysanthemum plant of the decorative class, which was originated by me by crossing the chrysanthemum variety known as "Towhee" (Plant Patent No. 1,169) with itself.

The primary objective of this breeding was to produce a new chrysanthemum variety having an early blooming habit, combined with the strong plant characteristics of the parent variety "Towhee," but which bears red flowers. This objective was fully achieved along with other desirable improvements, as evidenced by the following unique combination of characteristics which are outstanding in the new variety and distinguish it from its parents, as well as from all other varieties of which I am aware:

(1) A strong and upright habit of growth;
(2) An early blooming habit;
(3) Relatively thick flowers;
(4) A pointed flower petal form;
(5) A distinctive, attractive and sharp general color tonality of the flowers corresponding to Scarlet, overcast with Scarlet-Red.

Asexual reproduction of the new variety by both top cuttings and underground runners, as performed at Newark, New York, shows that the foregoing characteristics and distinctions come true to form and are established and transmitted through succeeding propagations.

The accompanying drawing shows typical specimens of the vegetative growth and flowers of my new chrysanthemum variety in different stages of development and as depicted in color as nearly true as it is reasonably possible to make the same in a color illustration of this character, as well as a typical specimen stem which is depicted in blank and white for the purpose of illustrating the form and habit of growth of the plant.

The following is a detailed description of the new variety, with color terminology in accordance with Ridgway's Color Standards and Nomenclature:

Parentage: Seedling.
*Seed parent.*—"Towhee."
*Pollen parent.*—Self.
Classification: Decorative.
Growth: 2½ feet tall; upright.
Locations where observations made: Outdoors at Newark, New York, in the early morning during the early part of October.

Cold Resistance: Plant is winter hardy in northern New York State.
Blooming period: In Newark, New York, climatic area, bloom begins in early September and continues until frost.

*Flower*

Bud:
*Color.*—When petals first divide—Vinaceous-Rufous, Plate 14. When petals begin to unfurl—Scarlet-Red, Plate 1, very lightly overcast with Dragon's-Blood Red, Plate 13. When half-blown: Inside—Brazil Red, Plate 1, lightly overcast with Nopal Red, Plate 1; outside—Pompeian Red, Plate 13.
*Peduncle.* — Color — Absinthe Green, Plate 31. Strength—strong.

Bloom:
*Size.*—5½ inches in diameter.
*Stem.*—Strong.
*Form.*—Thick decorative; about 2 inches thick.
*Petalage.*—Pointed and long.
*Color.*—Center of flower—Nopal Red, Plate 1, very lightly overcast with Scarlet-Red, Plate 1. Outer petals—Scarlet, Plate 1, lightly overcast with Scarlet-Red, Plate 1. Base of petals—Strontian Yellow, Plate 16. Inside of petals—Scarlet, Plate 1, overcast with Scarlet-Red, Plate 1. Reverse of petals—Dragon's-Bloom Red, Plate 13, very lightly overcast with Nopal Red, Plate 1.
*Petals.*—Texture—thin. Form—pointed.
*Fragrance.*—Characteristic chrysanthemum.

*Plant*

Form: Upright.
Growth: Strong.
Foliage:
*Size.*—Medium; leaves extend to the ground.
*Quantity.*—Moderate.
*Color.*—Upper side—Forest Green, Plate 17. Reverse side—Absinthe Green, Plate 31.
*Texture.*—Leathery.

I claim:

A new and distinct variety of chrysanthemum plant of the decorative class, substantially as herein shown and described, characterized particularly as to novelty by the unique combination of a strong and upright habit of growth, an early blooming habit, relatively thick flowers, a pointed flower petal form, a distinctive, attractive and sharp general color tonality of the flowers corresponding to Scarlet, overcast with Scarlet-Red.

No references cited.

ABRAHAM G. STONE, *Primary Examiner.*
R. E. BAGWILL, *Assistant Examiner.*